(12) United States Patent
Woodward et al.

(10) Patent No.: US 8,366,895 B2
(45) Date of Patent: Feb. 5, 2013

(54) DIFFERENTIAL PH PROBE

(75) Inventors: John Robert Woodward, Windsor, CO (US); Leon Edward Moore, Windsor, CO (US); Kevin James West, Loveland, CO (US)

(73) Assignee: Hach Company, Loveland, CO (US)

( * ) Notice: Subject to any disclaimer, the term of this patent is extended or adjusted under 35 U.S.C. 154(b) by 1382 days.

(21) Appl. No.: 11/516,186

(22) Filed: Sep. 6, 2006

(65) Prior Publication Data
US 2007/0221498 A1 Sep. 27, 2007

Related U.S. Application Data

(60) Provisional application No. 60/785,339, filed on Mar. 23, 2006.

(51) Int. Cl.
*G01N 27/26* (2006.01)
(52) U.S. Cl. .......... 204/433; 204/435; 324/428
(58) Field of Classification Search .......... 204/400–435; 205/787.5; 436/68
See application file for complete search history.

(56) References Cited

U.S. PATENT DOCUMENTS

| | | | | |
|---|---|---|---|---|
| 4,003,705 A | * | 1/1977 | Buzza et al. | 436/68 |
| 4,128,468 A | | 12/1978 | Bukamier | |
| 4,196,383 A | | 4/1980 | Teass, Jr. | |
| 4,657,657 A | * | 4/1987 | Stellmacher | 204/400 |
| 6,221,222 B1 | * | 4/2001 | Kipp et al. | 204/435 |
| 6,395,158 B1 | * | 5/2002 | King et al. | 204/420 |
| 2003/0047453 A1 | * | 3/2003 | Barben et al. | 204/435 |
| 2003/0150726 A1 | | 8/2003 | West | |
| 2005/0082167 A1 | * | 4/2005 | Iwamoto et al. | 204/433 |

FOREIGN PATENT DOCUMENTS

| | | |
|---|---|---|
| DE | 3732324 A | 6/1989 |
| DE | 10315161 A | 10/2004 |
| GB | 2088565 A | 6/1982 |

OTHER PUBLICATIONS

OMEGA pH Differential Sensor PHE-6028-PO Operator's Manual, 1995.*

* cited by examiner

*Primary Examiner* — Keith Hendricks
*Assistant Examiner* — Bach Dinh
(74) *Attorney, Agent, or Firm* — Ference & Associates LLC

(57) ABSTRACT

A differential pH probe design uses a container having an outer surface and an inner volume, where the inner volume is divided into a first chamber and a second chamber. A first pH-sensitive area is located on the outer surface of the first chamber where the first pH-sensitive area is configured to be exposed to a sample. A second pH-sensitive area is located on the outer surface of the second chamber where the second pH-sensitive area is shielded from the sample and is exposed to a buffer solution. A first electrode is configured to detect a first voltage in the first chamber and a second electrode is configured to detect a second voltage in the second chamber. Circuitry is coupled to the first and second electrodes and configured to process the first voltage and the second voltage to determine a pH of the sample.

29 Claims, 7 Drawing Sheets

US 8,366,895 B2

DIFFERENTIAL PH PROBE

RELATED APPLICATIONS

This application claims the benefit of U.S. provisional application No. 60/785,339 filed on Mar. 23, 2006 entitled "Differential pH probe," which is hereby incorporated by reference into this application.

BACKGROUND OF THE INVENTION

The invention is related to the field of pH measurements, and in particular, to a differential pH probe. A pH probe typically operates using an active chamber that measures a voltage across a pH sensitive material immersed in a sample. Differential pH sensors also use a reference chamber that measures a voltage across a pH sensitive material immersed in a buffer solution having a known pH, typically with a pH of 7. The differential probe uses the active voltage and the reference voltage to determine the pH of the sample. Current pH probes are typically complex designs with many fluid seals and may be large and costly to manufacture.

DETAILED DESCRIPTION OF THE PREFERRED EMBODIMENT

FIGS. 1-7 and the following description and exhibits depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
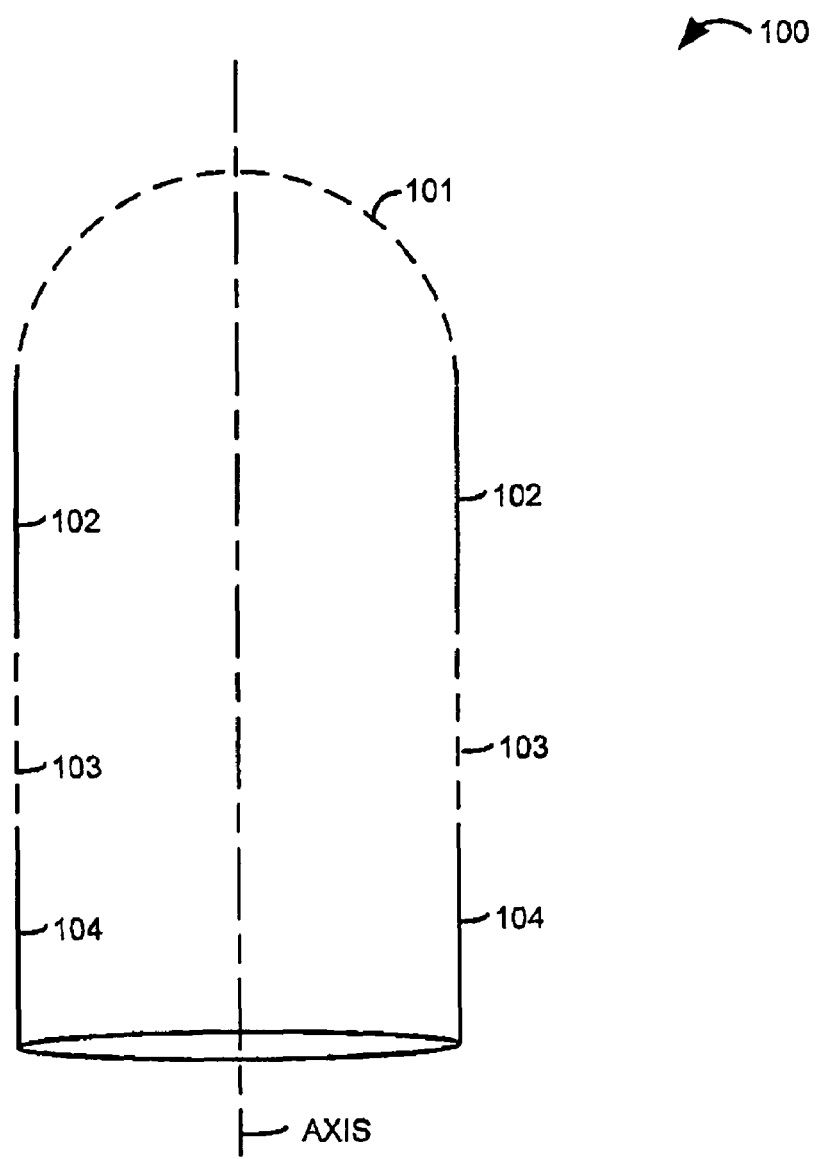
FIG. 1 illustrates glass piece 100 used in differential pH probe 150, in an example embodiment of the invention.

FIG. 1 illustrates glass piece 100 used in differential pH probe 150 (shown in FIG. 4), in an example embodiment of the invention. Glass piece 100 is depicted as a tube, although other suitable shapes could be used. A generalized cylinder is a cylinder where the cross section can be any shape. Glass piece 100 includes active areas 101 and 103, in addition to, non-active areas 102 and 104. Active areas 101 and 103 are formed by pH sensitive glass. An example of pH-sensitive glass is lithium-ion conductive glass. Non-active areas 102 and 104 are formed by non-pH sensitive glass. Note that alternative materials other than glass could be used for piece 100, such as pH-sensitive polymers and plastics.

Note that both the active and non-active areas are integrated together to form a single piece of glass—glass piece 100. This integration could be accomplished by treating a single glass tube to form the active and non-active areas. Alternatively, the active and non-active areas could be formed separately from one another and then fused together to form glass piece 100.

Note that active areas 101 and 103 share the same axis making them co-axial with one another. The co-axial configuration allows for a large active area 101 while reducing the overall size of probe 150. The single piece configuration provides structural strength and requires fewer seals than a multiple piece configuration.

Figure 2:
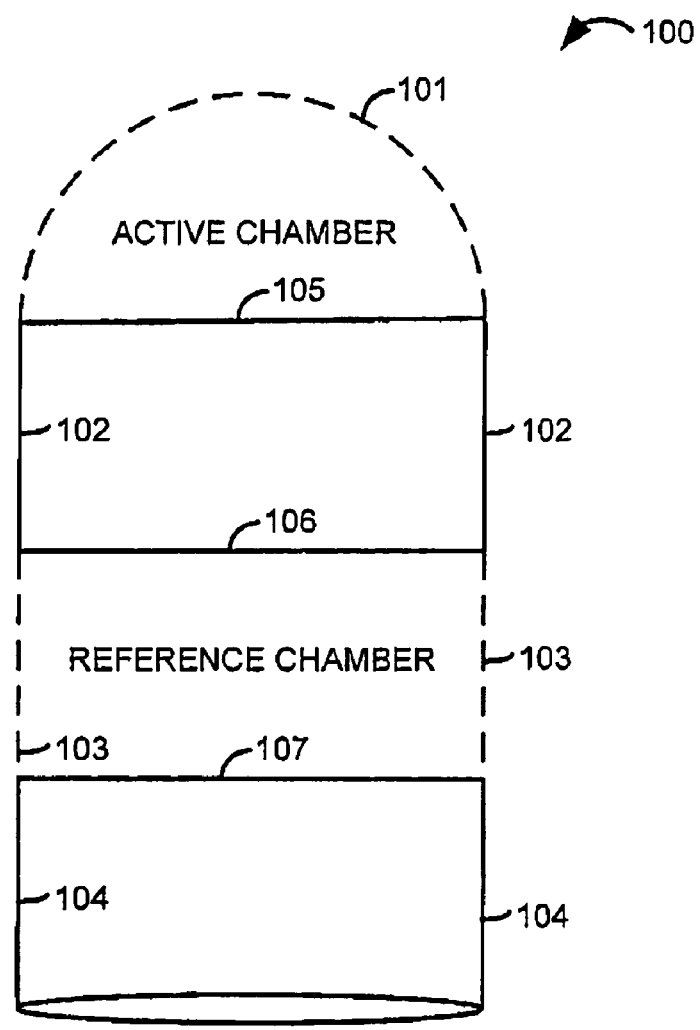
FIG. 2 illustrates glass piece 100 with seals, in an example embodiment of the invention.

FIG. 2 illustrates glass piece 100 from FIG. 1, in an example embodiment of the invention. Glass piece 100 now has seals 105, 106, and 107. Seals 105-107 could be rubber, silicon, or some other suitable insulating material. Active area 101 and seal 105 form a first chamber referred to as the active chamber. Active area 103 and seals 106-107 form second chamber referred to as the reference chamber. Both the active and reference chambers are filled with an electrolyte solution. In one example embodiment of the invention, glass piece 100 may be called a container that is divided into a number of different chambers.

Figure 3:
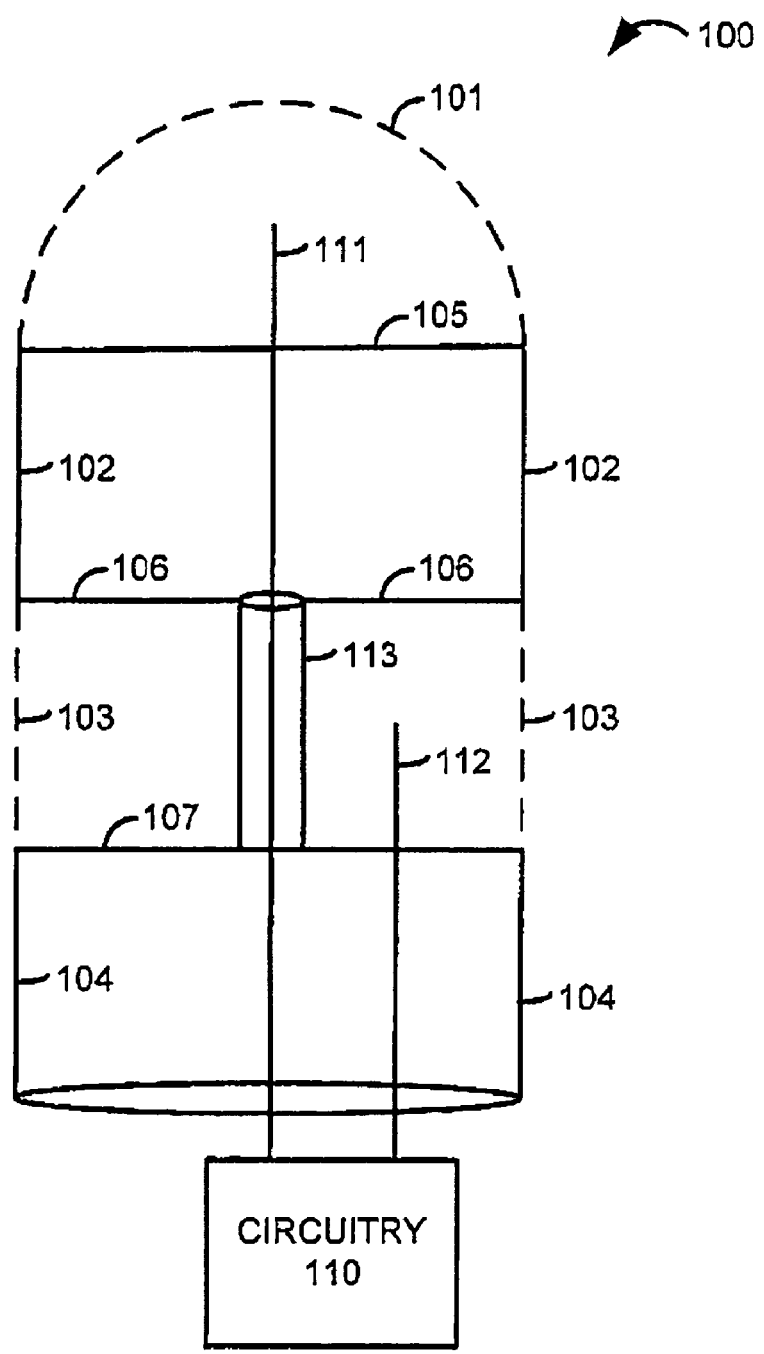
FIG. 3 illustrates glass piece 100 with seals and circuitry, in an example embodiment of the invention.

FIG. 3 illustrates glass piece 100 from FIG. 2 and also shows circuitry 110. Glass piece 100 includes active electrode 111 that is exposed within the active chamber and then runs to circuitry 110. Note that insulating tube 113 is used so that active electrode 111 runs through the center of the reference chamber, but is not exposed within the reference chamber. Glass piece 100 also includes reference electrode 112 that is exposed within the reference chamber and then runs to circuitry 110.

Figure 4:
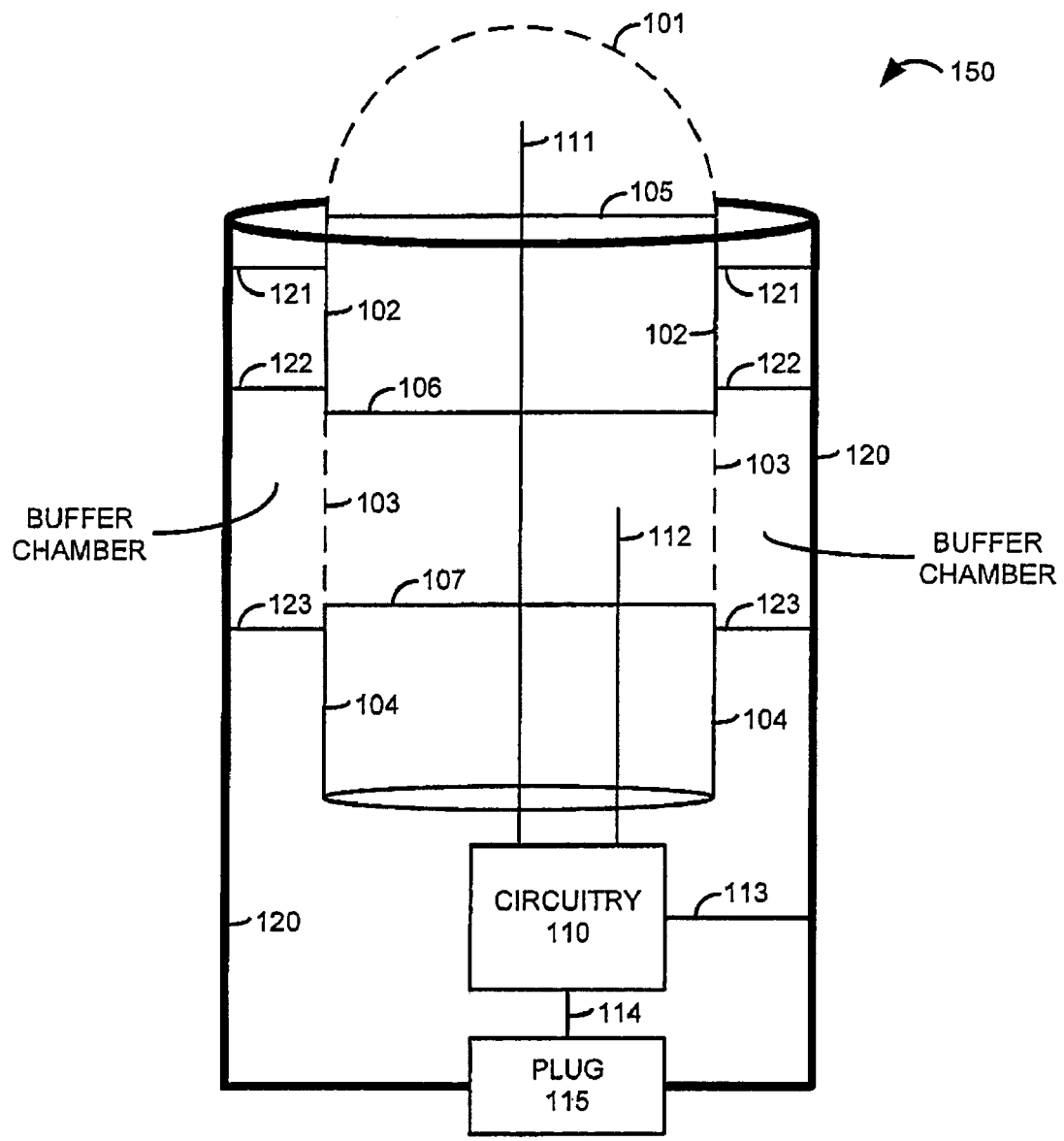
FIG. 4 illustrates differential pH probe 150, in an example embodiment of the invention.

FIG. 4 illustrates differential pH probe 150 in an example of the invention. Probe 150 includes glass piece 100 and circuitry 110 as described in FIGS. 1-3. Probe 150 also includes conductive enclosure 120. Conductive enclosure 120 could be tube-shaped like glass piece 100, although other shapes could be used. Glass piece 100 and circuitry 110 are placed within conductive enclosure 120.

Conductive enclosure 120 includes seals 121, 122, and 123. In this example with glass piece 100 and enclosure 120 being tube-shaped, seals 121-123 could be doughnut-shaped discs, although other shapes could be used in other examples. These disks could have much larger contact areas than conventional o-rings to provide better seals. Seals 121-123 could be rubber, silicon, or some other insulating material. Seals 121-122 provide a junction that allows electrical conductivity, but not fluid transfer, between the buffer chamber and the sample being tested. To provide this junction, seals 121-122 could be silicon disks with ceramic frits (tubes), where seals 121-122 are separated by a salt gel to form a salt bridge.

Seal 121 seals the end of enclosure 120 so that active area 101 of the active chamber may remain exposed to an external sample, but so that the external sample will not enter enclosure 120. Enclosure 120, seals 122-123, and active area 103 form a buffer chamber around active area 103 of glass piece 100. This buffer chamber is filled with a buffer solution that maintains a constant pH—typically seven.

Circuitry 110 is grounded to conductive enclosure 120 by electrical line 113. Circuitry 110 is coupled to plug 115 by electrical lines 114. Thus, circuitry 110 communicates with external systems through lines 114 and plug 115. In other embodiments, circuitry 110 may communicate with an external system using a wireless or non-contact technology, for example an optical link or an RF link.

In operation, active area 101 of probe 150 is dipped into the sample whose pH will be determined. Note that seal 121 prevents the sample from entering enclosure 120. The sample (with unknown pH) interacts with active area 101 to produce a first voltage across active area 101. This first voltage is referred to as the active voltage and corresponds to the unknown pH of the sample. Active electrode 111 detects the active voltage and indicates the active voltage to circuitry 110.

In a similar manner, the buffer solution (with known pH) interacts with active area 103 to produce a second voltage across active area 103. This second voltage is referred to as the reference voltage and corresponds to the known pH of the buffer solution. Reference electrode 112 detects the reference voltage and indicates the reference voltage to circuitry 110.

Circuitry 110 processes the active and reference voltages in the conventional manner to determine the pH of the sample. Circuitry 110 indicates the pH of the sample to external systems (not shown) that are plugged into plug 115.

Conductive enclosure 120 is typically held by hand during testing. Note that conductive enclosure 120 electrically shields the internal components of probe 150 (electrodes 111-112, circuitry 110) from hand capacitance. Conductive enclosure 120 also provides a ground. Note that conductive enclosure 120 could be stainless steel, aluminum, or some other conductive material. In one example embodiment of the invention, conductive enclosure 120 may have a conducting part and a non-conducting part. The conductive part would begin just below seal 123 and would cover and shield the lower portion of the probe, including the circuitry 110. The upper portion starting just below seal 123 would be made from a non-conductive material or have a non-conductive coating. When using the two part enclosure a separate ground rod may be located in the outer salt bridge seal 121.

Figure 5:
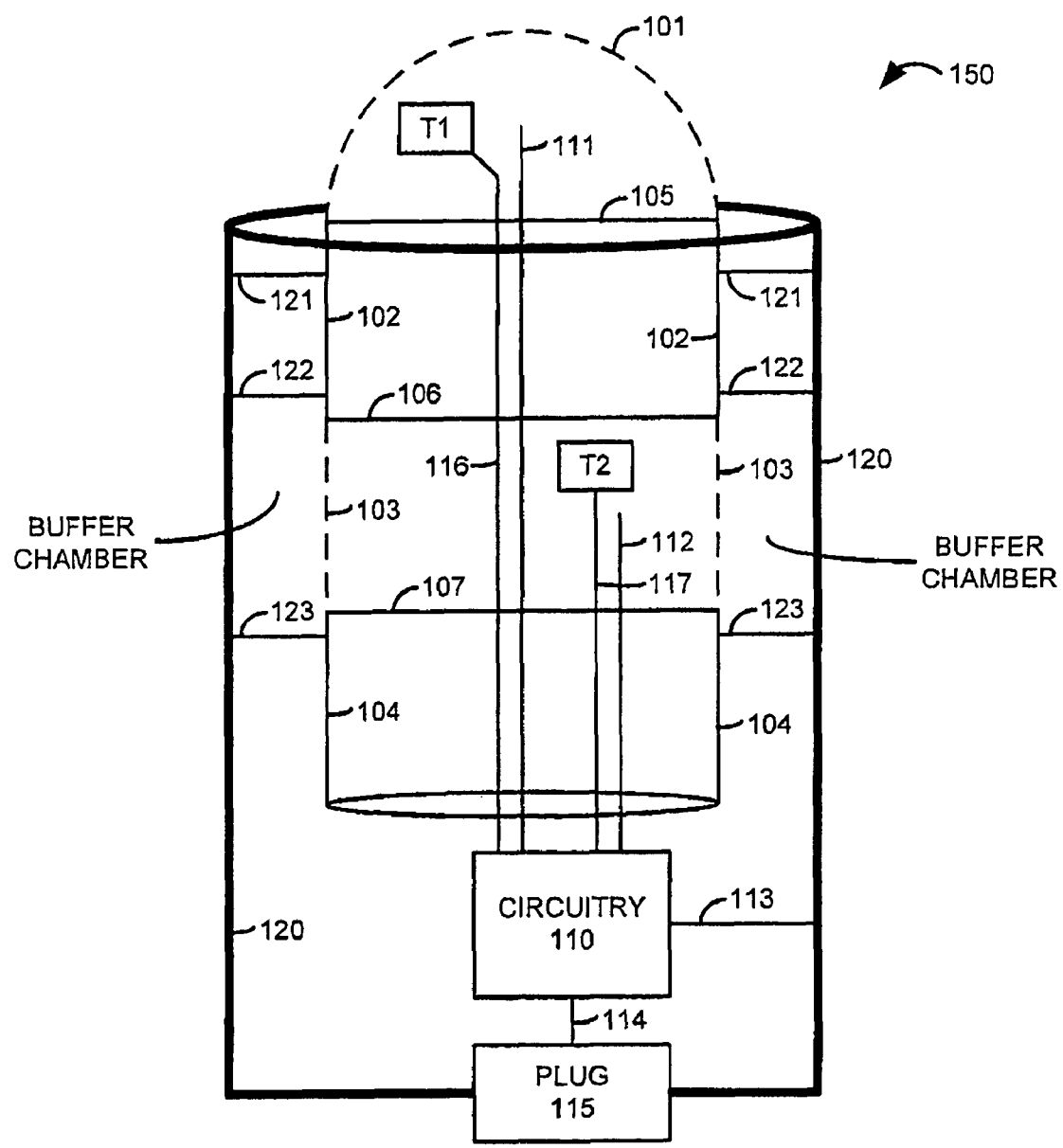
FIG. 5 illustrates differential pH probe 150 with temperature sensors, in an example embodiment of the invention.

FIG. 5 illustrates differential pH probe 150 in an example of the invention. Thermistor T1 has been added to the active chamber to detect the temperature near active electrode 111. Thermistor T2 has been added to the reference chamber to detect the temperature near reference electrode 112. Thermistors T1 and T2 could be integrated within seals 105-107. Thermistor T1 transfers its temperature information to circuitry 110 over electrical line 116. Thermistor T2 transfers its temperature information to circuitry 110 over electrical line 117. Circuitry processes the temperature information from thermistors T1 and T2 to provide temperature compensation during the pH determination. In another embodiment of the invention, thermistor T1 may be located on the outside of the active chamber (not shown) and be exposed to the sample and used to detect the temperature of the sample. In another embodiment of the invention, thermistor T2 may be located in the buffer chamber.

Figure 6:
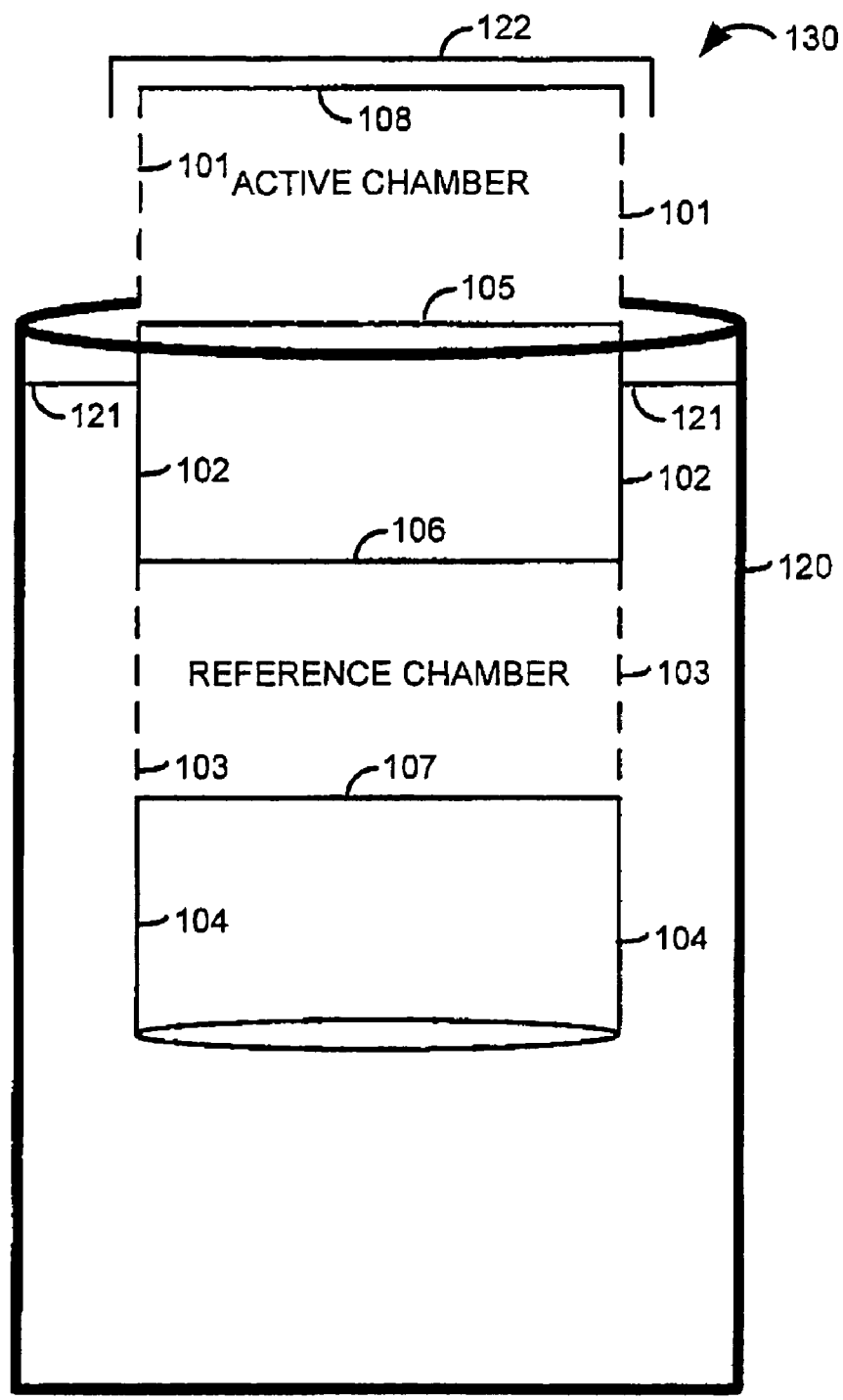
FIG. 6 illustrates glass piece 130 used in a differential pH probe in an example embodiment of the invention.

FIG. 6 illustrates an alternative to glass piece 100. Note that some details from the previous figures are omitted for clarity. Glass piece 130 is now used for probe 150 instead of glass piece 100. Glass piece 130 is similar to glass piece 100 with active areas 101 and 103 and non-active areas 102 and 104 separated by seals 105-107 to form the active and reference chambers. The variation from glass piece 100 is in the shape of the active chamber. Active area 101 is no longer a dome at the top of the glass piece, but is now formed by the walls of glass piece 130 in the same way that active area 103 forms the reference chamber. Thus, the active chamber has the same geometry as the reference chamber. Non-active glass 108 is used at the top of the active chamber, although a seal could be used instead of non-active glass 108 if desired. The top of the active chamber is protected by cap 122. Cap 122 could be rubber, metal, or some other protective material that is adhered to glass piece 130.

Figure 7:
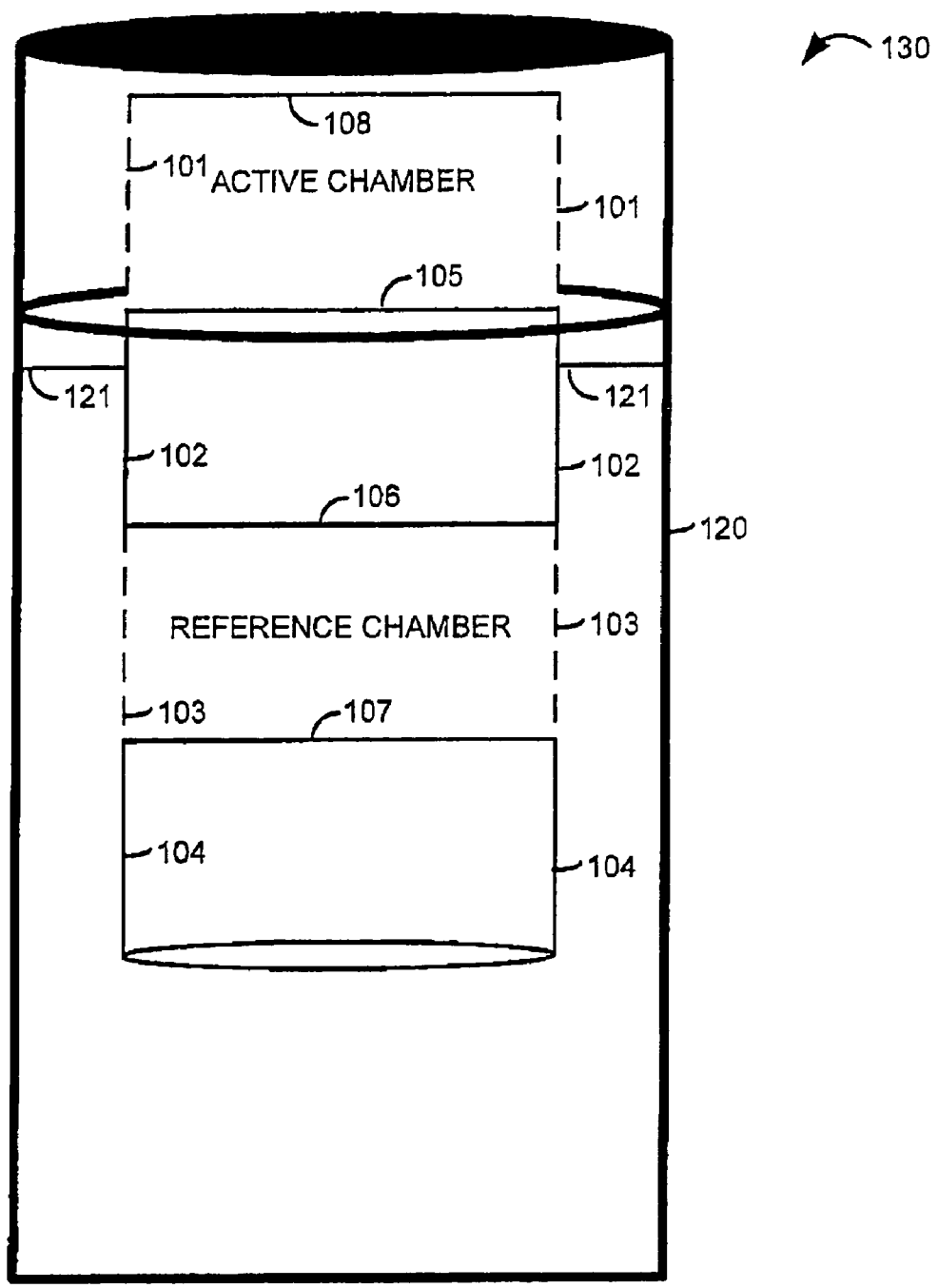
FIG. 7 illustrates a variation for conductive enclosure 120 in another example embodiment of the invention.

FIG. 7 illustrates a variation for conductive enclosure 120. Note that some details from the previous figures are omitted for clarity. Glass piece 130 is used, but glass piece 100 could be used as well. Enclosure 120 now extends above the active chamber of glass piece 130 to provide protection. The extension of enclosure 120 must still allow the sample to contact active area 101, so openings in enclosure 120 should be provided for this purpose. The sample should still not be allowed to pass seal 121.

We claim:

1. A differential pH probe, comprising:
    a container formed of a container material and having an outer surface and an inner volume, where the inner volume is divided into a first chamber and a second chamber;
    a first pH-sensitive container material area on a first chamber outer surface where the first pH-sensitive container material area is configured to be exposed to a sample;
    a second pH-sensitive container material area on a second chamber outer surface where the second pH-sensitive container material area is shielded from the sample and is exposed to a buffer solution;
    a first electrode configured to detect a first voltage in the first chamber; and
    a second electrode configured to detect a second voltage in the second chamber;
    wherein the outer surface of the container is contiguous container material that includes the first pH-sensitive container material area and the second pH-sensitive container material area.

2. The differential pH probe of claim 1 where the container has a generalized cylindrical shape.

3. The differential pH probe of claim 2 where the first chamber is formed by one end of the generalized cylindrical shape and a first seal and the second chamber is formed by a middle section of the generalized cylindrical shape and a second and third seal.

4. The differential pH probe of claim 1 where the first pH-sensitive container material area forms a first shape and the second pH sensitive container material area forms a second shape and where the first shape and the second shape are substantially co-axial.

5. The differential pH Probe of claim 1 where the first pH-sensitive container material area is generally dome shaped and formed at a first end of the container.

6. The differential pH probe of claim 1 where the first pH-sensitive container material area forms a first cylindrical shape and the second pH-sensitive container material area forms a second cylindrical shape.

7. The differential pH probe of claim 6 where the first and second cylindrical shapes have the same diameter.

8. The differential pH probe of claim 1 further comprising:
    a third chamber where the third chamber is between the first and second chambers and a third chamber outer surface formed of a non-pH-sensitive container material.

9. The differential pH probe of claim 1 further comprising:
    circuitry coupled to the first and second electrodes and configured to process the first voltage and the second voltage to determine a pH of the sample; and
    a conductive enclosure where the conductive enclosure surrounds at least part of the outer surface of the container and where the conductive enclosure is coupled to a ground path in the circuitry.

10. The differential pH probe of claim 9 further comprising:
a first seal and a second seal where the first and second seals couple to the outer surface of the container and an inner surface of the conductive enclosure to form a compartment that holds the buffer solution.

11. The differential pH probe of claim 10 where the compartment that holds the buffer solution is axially aligned with the first chamber.

12. The differential pH probe of claim 1 further comprising:
circuitry coupled to the first and second electrodes and configured to process the first voltage and the second voltage to determine a pH of the sample;
a first temperature sensor couple to the circuitry and configured to sense the temperature in the first chamber; and
a second temperature sensor coupled to the circuitry and configured to sense the temperature in the second chamber and where the circuitry is configured to compensate the determined pH for the temperature sensed in the first and second chambers.

13. The differential pH probe of claim 1 further comprising circuitry coupled to the first and second electrodes and configured to process the first voltage and the second voltage to determine a pH of the sample.

14. The differential pH probe of claim 1, wherein the first pH-sensitive container material area and the second pH-sensitive container material area are concentric.

15. A differential pH probe, comprising:
a generalized cylindrical container formed of a container material and having an outer surface and an inner volume, where the inner volume is divided into a first chamber at a first end, a second chamber adjacent to the first chamber and a third chamber adjacent to the second chamber;
a first part of a first chamber outer surface comprising a first pH-sensitive container material area configured to be exposed to a sample;
a second outer surface formed of a non-pH-sensitive container material;
a first part of a third chamber outer surface comprising a second pH-sensitive container material area where the second pH-sensitive container material area is immersed in a buffer solution;
a first electrode configured to detect a first voltage in the first chamber; and
a second electrode configured to detect a second voltage in the third chamber;
wherein the outer surface of the container is contiguous container material that includes the first pH-sensitive container material area and the second pH-sensitive container material area.

16. The differential pH probe of claim 15 further comprising:
a first seal forming a boundary between the first chamber and the second chamber;
a second seal inserted into the generalized cylindrical container and forming a boundary between the second chamber and the third chamber; and
a third seal inserted into the generalized cylindrical container and forming an outer boundary of the third chamber.

17. The differential pH probe of claim 15 where a cross section of the generalized cylindrical shape is selected from one for the following: circle, square, rectangle, regular polygon, star polygon, ribbed circle, rounded rectangle, oval, spline, and ellipse.

18. The differential pH probe of claim 15 where the first end of the generalized cylindrical shape is generally dome shaped and forms the first pH-sensitive container material area.

19. The differential pH probe of claim 15 further comprising:
circuitry coupled to the first and second electrodes and configured to process the first voltage and the second voltage to determine a pH of the sample; and
a conductive enclosure where the conductive enclosure surrounds the second and third chambers and where the conductive enclosure is coupled to a ground path in the circuitry.

20. The differential pH probe of claim 19 further comprising:
a first seal and a second seal where the first and second seals couple to the outer surface of the generalized cylindrical shape and an inner surface of the conductive enclosure to form a compartment that holds the buffer solution.

21. The differential pH probe of claim 15 further comprising:
circuitry coupled to the first and second electrodes and configured to process the first voltage and the second voltage to determine a pH of the sample;
a first temperature sensor coupled to the circuitry and configured to sense the temperature of the sample; and
a second temperature sensor coupled to the circuitry and configured to sense the temperature in the third chamber and where the circuitry is configured to compensate the determined pH for the temperature sensed in the sample and the third chambers.

22. The differential pH probe of claim 15 where the buffer solution has a pH of 7.

23. The differential pH probe of claim 15 where the first chamber has a different shape than the third chamber.

24. The differential pH probe of claim 15 where the first chamber has a different diameter than the third chamber.

25. The differential pH probe of claim 15 where the first chamber and the third chamber are axially aligned.

26. The differential pH probe of claim 15 further comprising circuitry coupled to the first and second electrodes and configured to process the first voltage and the second voltage to determine a pH of the sample.

27. A method of manufacturing a differential pH probe, comprising:
forming a tube of a tube material with two rings of pH sensitive tube material and two rings of non-pH sensitive tube material where the tube has alternating rings of pH sensitive tube material and non-pH sensitive tube material and where the tube has a closed end and where a first ring of pH sensitive tube material is at the closed end;
dividing the tube into a first, a second and a third chamber where the first chamber corresponds to the first ring of pH sensitive tube material, the second chamber corresponds to a first ring of non-pH sensitive tube material, and the third chamber corresponds to a second ring of pH sensitive tube material;
inserting a first electrode into the first chamber and a second electrode into the third chamber and connecting the first and second electrodes to circuitry; and
immersing the second ring of pH sensitive tube material in a buffer solution;
wherein the tube of material is contiguous material that includes the first pH-sensitive tube material and the second pH-sensitive tube material.

28. The method of manufacturing a differential pH probe of claim 27, further comprising:
surrounding the second and third chambers with a conductive enclosure and connecting a ground path in the circuitry to the conducting enclosure.

29. The method of manufacturing a differential pH probe of claim 27, further comprising:
inserting a first temperature sensor into the first chamber and a second temperature sensor into the third chamber and connecting the first and second temperature sensors to the circuitry.

* * * * *